(12) United States Patent
Von Haeften et al.

(10) Patent No.: US 9,931,607 B2
(45) Date of Patent: Apr. 3, 2018

(54) CHEMICAL REACTION BY COMBINATION OF GAS-PHASE AND WET-CHEMICAL METHODS

(71) Applicant: Gediminas Galinis, London (GB)

(72) Inventors: Klaus Von Haeften, Leicester (GB); Gediminas Galinis, London (GB)

(73) Assignee: Gediminas Gallinis, London (GB)

( * ) Notice: Subject to any disclaimer, the term of this patent is extended or adjusted under 35 U.S.C. 154(b) by 757 days.

(21) Appl. No.: 14/381,338

(22) PCT Filed: Feb. 28, 2013

(86) PCT No.: PCT/GB2013/050498
§ 371 (c)(1),
(2) Date: Aug. 27, 2014

(87) PCT Pub. No.: WO2013/128193
PCT Pub. Date: Sep. 6, 2013

(65) Prior Publication Data
US 2015/0037260 A1    Feb. 5, 2015

(30) Foreign Application Priority Data

Feb. 28, 2012 (GB) .................................. 1203430.2

(51) Int. Cl.
*B01J 3/00* (2006.01)
*B01J 4/00* (2006.01)
(Continued)

(52) U.S. Cl.
CPC .............. *B01J 3/006* (2013.01); *A61K 49/005* (2013.01); *B01J 4/002* (2013.01); *B01J 19/24* (2013.01);
(Continued)

(58) Field of Classification Search
CPC ...... B01J 3/006; B01J 3/02; B01J 4/002; B01J 19/24; B01J 19/26
See application file for complete search history.

(56) References Cited

U.S. PATENT DOCUMENTS 5,665,277 A    9/1997   Johnson
5,770,022 A    6/1998   Chang
(Continued)

FOREIGN PATENT DOCUMENTS

JP         2007162133      6/2007
KR     1020107009640      4/2010
(Continued)

OTHER PUBLICATIONS

Brewer, et al., "In situ passivation and blue luminescence of silicon clusters using a cluster beam/water codeposition production method", Applied Physics Lttrs., 94:261102 (2009).
(Continued)

*Primary Examiner* — Lessanework Seifu
(74) *Attorney, Agent, or Firm* — Pabst Patent Group LLP

(57) ABSTRACT

The invention provides a new apparatus (20) and method for producing entirely new types of nanoparticles exhibiting novel properties. The apparatus comprises a vacuum chamber (22) containing a gas and feed means (1) for feeding a liquid jet (26) into the chamber and through the gas. The invention extends to the new types of nanoparticles per se, and to uses of such nanoparticles in various biomedical applications, such as in therapy and diagnosis, as well as in opto-electronics.

22 Claims, 8 Drawing Sheets

(51) Int. Cl.
*B01J 19/24* (2006.01)
*A61K 49/00* (2006.01)
*C01B 33/02* (2006.01)
*C09K 11/59* (2006.01)
*C23C 14/34* (2006.01)
*H01J 37/34* (2006.01)

(52) U.S. Cl.
CPC .............. *C01B 33/02* (2013.01); *C09K 11/59* (2013.01); *C23C 14/34* (2013.01); *H01J 37/34* (2013.01); *H01J 37/3464* (2013.01); *B01J 2204/002* (2013.01); *B01J 2219/00085* (2013.01); *B01J 2219/00137* (2013.01); *C01P 2006/60* (2013.01); *H01J 2237/002* (2013.01); *Y10T 428/2982* (2015.01)

(56) References Cited

U.S. PATENT DOCUMENTS

| | | | |
|---|---|---|---|
| 7,758,668 | B1 | 7/2010 | Wu |
| 2003/0143151 | A1 | 7/2003 | Diener |
| 2005/0200648 | A1* | 9/2005 | Doak .......................... B41J 2/02 347/21 |
| 2006/0043319 | A1* | 3/2006 | Gaebel .................. H05G 2/003 250/504 R |
| 2009/0250641 | A1 | 10/2009 | Moriya |
| 2010/0206720 | A1 | 8/2010 | Lin |
| 2010/0243753 | A1* | 9/2010 | Doak .................... B05B 7/0475 239/11 |

FOREIGN PATENT DOCUMENTS

| | | |
|---|---|---|
| WO | 2005066069 | 7/2005 |
| WO | 2006043656 | 4/2006 |
| WO | 2009091416 | 7/2009 |

OTHER PUBLICATIONS

Faubel, et al., "A molecular beam study of the evaporation of water from a liquid jet", Atoms, Molecule, Clusters, 10:269-77 (1988).
Torricelli, et al., "Size-selecting effect of water on fluorescent silicon clusters", Nanotechnology, 22(31):315711 (2011).
Von Haeften, et al., "A novel approach towards the production of luminescent silicon nanoparticles: sputtering, gas aggregation and co-deposition with H2O", Eu Physical J, 52:11-4 (2009).
International Search Report and Written Opinion for corresponding PCT application PCT/GB2013/050498 dated Jul. 30, 2013.
Chinese Office Action for corresponding Chinese application 201380019606.3 dated Aug. 14, 2015 with English Translation.
Japanese Office Action for corresponding Japanese application JP2014-559293 dated Nov. 1, 2016 with English Translation.
United Kingdom Search Report for application GB1203430.2 dated Jun. 29, 2012.

* cited by examiner

CHEMICAL REACTION BY COMBINATION OF GAS-PHASE AND WET-CHEMICAL METHODS

The invention relates to chemical reactions, and in particular to a method and apparatus for producing nanoparticles (NPs). In particular, the invention relates to an apparatus and method for producing entirely new types of nanoparticles exhibiting novel properties. The invention extends to these new types of nanoparticles per se, and to uses of such nanoparticles in various biomedical applications, such as in therapy and diagnosis, as well as in opto-electronics.

Nanoparticles are aggregates that comprise between 2 and up to about $10^9$ atoms or molecules. They often have properties which are distinct from atoms and molecules, with abrupt variations in nanoparticle properties being observed in the quantum size regime (<100 atoms) when even just one atom is added. At larger sizes (>100 atoms), the properties change gradually with further increases in size, such that bulk properties begin to emerge. This size dependence means that novel materials with very controlled properties should be possible, if the size can be sufficiently well controlled.

Nanoparticle (NP) research is currently an area of intense scientific interest due to a wide variety of potential applications in biomedical, optical and electronic fields. For example, silicon NPs have attracted attention due to their relevance in microelectronics and, more recently, for use as light emitters. One idea is to replace electrical signal transmission with optical signal transmission in microelectronics using nanoparticles. Unfortunately, crystalline silicon is a very inefficient light emitter due to its indirect band gap. Silicon NPs, in contrast, have a quasi-direct band gap due to their small size and are, therefore, able to emit light efficiently. Another idea is to use nanoparticles to enhance the energy conversion of solar cells, many of which are made of silicon. Fluorescent NPs also have potential uses in medical diagnostics and therapy. Fluorescent NPs of silicon are particularly promising because silicon-based NPs are regarded as being non-toxic and are suitable for in vivo applications.

There are several methods for creating NPs, which can be classified into bottom-up and top-down methods, depending upon whether nanoparticles are built from small units or by breaking-up larger units. Bottom-up methods can be further classified into gas-phase based or wet-chemical based methods. These methods differ in how the physical and chemical properties of the nanoparticles to be produced can be controlled. They are also distinguished by the production rates that can be achieved.

All bottom-up methods require the provision of starting materials in the form of atoms or molecules which then react and grow into nanoparticles. In order to grow into nanoparticles the atoms or molecules need to nucleate, which in the gas phase, for example, can only happen at a critical density when the atoms or molecules undergo three-body collisions to release excess binding energy. In gas phase methods a condensation medium is often provided, for instance an inert buffer gas which mediates the three-body collisions (gas-aggregation method, K. Sattler, J. Muhlbach, E. Recknagel, Phys. Rev. Lett. 45(10), 821 (1980)) or a surface is provided upon which the atoms or molecules condense, diffuse, aggregate and react, releasing the excess energy into the surface. As an example, pure metal or semiconductor vapours generated by ion sputtering do not reach the critical densities needed for aggregation and the production of nanoparticles is impossible without introducing further means. Wet-chemical methods, on the other hand, do provide a straightforward medium for aggregation and reaction due to the high densities of liquids involved. In common wet-chemical methods, however, the number of nucleation centres gradually decreases once growth starts. The balance between growth rate and nucleation rate is, therefore, critical for the size. Small sizes require a large number of nucleation centres and high growth rates favour large sizes.

To limit the size of the nanoparticles further, growth needs to be inhibited at some point. This may be achieved by stopping supply of the atoms or molecules, as in gas-phase-based methods, or by reaching thermodynamic equilibrium conditions, as in wet-chemical methods. Moreover, practical use of nanoparticles requires chemical stabilisation, so as to inhibit further growth by physical aggregation or chemical transformation.

Both gas-phase and wet-chemical methods for the production of nanoparticles have specific advantages and limitations. In order to achieve the maximum range of control over nanoparticle properties there is, therefore, a need for an apparatus and associated method, which combines gas-phase and wet-chemical methods.

According to a first aspect, there is provided an apparatus for carrying out a chemical reaction, the apparatus comprising a vacuum chamber containing gas, and feed means for feeding a liquid jet into the vacuum chamber and through the gas, wherein, in use, atoms and/or molecules and/or atomic and/or molecular ions of the gas react with each other and/or with atoms and/or molecules of the liquid jet, to thereby form a reaction product.

In a second aspect, the invention provides a method for carrying out a chemical reaction, the method comprising:
  (i) providing a gas comprising atoms and/or molecules and/or atomic and/or molecular ions in a vacuum chamber;
  (ii) feeding a liquid jet comprising atoms and/or molecules into the vacuum chamber and through the gas; and
  (iii) allowing the atoms and/or molecules and/or atomic and/or molecular ions of the gas to react with each other and/or with the atoms and/or molecules of the liquid jet, so as to form a reaction product in the vacuum.

The inventors have found that it is surprisingly possible to carry out a chemical reaction (and produce nanoparticles) using the apparatus of the first aspect and the method of the second aspect, by combining a gas-phase and a wet chemical (i.e. the liquid jet) method. Previously, combining these two types of methods was difficult, because metal or semiconductor vaporisation techniques require a vacuum. At the low pressures required for the existence of a vacuum, most liquids cannot exist because the co-existence of liquid and gas phases is governed by the vapour pressure curve (as shown in FIG. 1 for water), which demonstrates that by whatever means liquid is introduced into a high or ultra-high vacuum, freezing at equilibrium conditions will usually occur. As described in the Examples, the inventors have developed an apparatus and a method which overcomes the aforementioned problem.

Being able to introduce and maintain liquids in a vacuum, as the inventors have done, advantageously allows chemical reactions to take place that previously could not have occurred. The new technology also makes it possible to de-couple reactive steps from each other, which, in turn, provides the degree of control necessary for the fabrication of multi-compound nanostructures where growth has to be limited to keep dimensions small. The inventors have found this degree of control unsurpassed by any pre-existing methods. In addition, the apparatus of the present invention can be employed on an industrial scale and, as such, achieves a very high throughput.

The vacuum used in the present invention may be generated in any standard vacuum chamber. The vacuum may be sufficient for the gas to be in the form of a vapour in the vacuum chamber. For example, the vacuum may be at a pressure of between about $10^{-12}$ and 1 mbar.

Metal vapours cannot be drawn from a gas cylinder because metals are solid under ambient conditions. Consequently, one has to vaporise the solids first, which is only possible in vacuum. Conversely, in wet-chemical methods the reactants are available as solutes, and, as such, the range of possibilities is limited by the availability of known solutes and by the limitations imposed by thermodynamics.

The gas may preferably be a vapour, i.e. substance in the gas phase at a temperature lower than its critical point, or a plasma. The gas may comprise atomic metal vapour, or semiconductor vapour, or molecular vapour, or cluster vapour comprising atomic or molecular aggregates/clusters, or an electron plasma, ionic plasma or ion vapour. The metal vapour used in the present invention may comprise or be formed from any metal, including a transition metal, a lanthanide or a noble metal.

The semiconductor vapour used in the present invention may be atomic, and may comprise or be formed from any semiconductor. For example, the semiconductor may be a group IV element, such as carbon, silicon, geranium, tin, lead, a group III element reacted with a group V element, such as BN, BP, AlN, GaN, GaP, GaSb, InN, InP, or a group II element reacted with a group VI element, such as ZnO, ZnS, ZnSe, CdS, CdSe or CdTe.

The molecular vapour used in the present invention may comprise $O_2$, $N_2$, CO, $CO_2$, $H_2O$, NaCl, $Mg_2O_2$, or $Al_2O_3$. The skilled reader will realise that this list is not complete, but purely illustrative.

The cluster vapour used in the present invention may comprise metal clusters such as $Fe_n$, $Ag_n$ or semiconductor clusters, such as $Si_n$, $(GaAs)_n$, $(CdS)_n$ etc., that have been pre-formed in another process. The skilled reader will realise that this list is not exhaustive, but rather illustrative.

The gas or vapour may be produced by heating, laser ablation, sputtering, arcs or discharges, each of which will be known to the skilled person.

The liquid jet may comprise or be formed from a polar or a non-polar solvent including water, acetic acid, pentane, hexane, heptane, cyclohexane, methanol, isopropanol, n-propanol, ethanol, dichloromethane, acetonitrile, dimethyl sulfoxide, toluene, chloroform, pyridine, benzene, hydrogen, nitrogen, helium, neon, argon, krypton or xenon. Those skilled in the art will realise that the aforementioned list is not a comprehensive list of liquids for use in the present invention, but rather an illustrative list. Preferably, though, the liquid jet comprises or is formed from water.

The hydrostatic pressure of the liquid jet may be up to about 200 bar, or up to 100 bar, preferably 40 bar, depending upon the capillary diameter and length. The liquid jet may comprise a solution or a suspension. One or more liquid jets or gases delivering different chemicals simultaneously may be fed into the vacuum chamber. Thus, the apparatus may comprise more than one liquid jet feed means.

The liquid jet may be charged. A charged liquid jet may exhibit deflection upon interaction with a sputter source electric field. This effect could be exploited to manipulate the jet's geometry or to attach or repel charged particles. The effect may be cancelled out, though, by providing a conduction path through the vacuum chamber or by controlled injection of charge directly into the liquid jet. Conversely, the apparatus of the present invention may utilise the jet as a conduction path.

The liquid jet may be operated or expelled in any orientation. For example, the liquid jet may flow substantially parallel or perpendicular with respect to the horizontal or any other angle in between. The jet may be orientated at an angle of about 0, 10, 20, 30, 40, 50, 60, 70, 80 or 90 degrees with respect to the horizontal. Gravity may deflect the jet. Hence, operating the jet which flows parallel to the horizontal forms a parabolic jet due to the action of gravity, but operating the jet perpendicularly (i.e. in a vertical plane) will negate this and allow a constant jet length at any jet velocity. As such, a substantially vertical flow may be preferred.

In one embodiment, the gas may form a continuous stream or jet. The apparatus may comprise means for collimating, channelling or lensing the gas to form a continuous stream, which may be aimed towards the path of the liquid jet. In embodiments where the diameter of the gas stream is less than the diameter of the liquid jet, the liquid is able to take up all of the gas with negligible wastage. For example, an evaporator fitted with collimating, channelling or lensing apparatus or a narrow aperture heat pipe may deliver a gas beam into the liquid jet. Accordingly, in this embodiment, the expression "through the gas" can mean contacting the liquid jet with the gas jet so that substantially all of the gas is taken up by the liquid.

Although the inventors do not wish to be bound by hypothesis, they believe that when an atom and/or molecule and/or atomic and/or molecular ion of the gas collides with the surface of the liquid jet it will be slowed down and become trapped due to the attractive forces of the liquid. Thereupon, the atom and/or molecule and/or atomic and/or molecular ion will diffuse until it encounters another atom and/or molecule and/or atomic and/or molecular ion with which it will react and form a diatomic molecule, thereby producing the reaction product, and completing the chemical reaction. Accordingly, when an ion or an electron collides with the liquid jet, the solvent molecules dissociate and react with ingredient solvent molecules or with dissociation fragments, thereby forming reaction products.

Depending on the reactivity, the atom and/or molecule and/or atomic and/or molecular ion may react with another atom and/or molecule and/or atomic and/or molecular ion of the gas or with an atom and/or molecule of the liquid jet. The atom and/or molecule and/or atomic and/or molecular ion may then react with a subsequent atom or atoms and/or molecule or molecules and/or atomic and/or molecular ions.

The liquid jet may be in the form of a liquid filament, which has a high surface area on which the gas may condense to form the reaction product. The liquid jet may be produced by passing liquid through a capillary, which may be achieved using turbulent flow or using co-flow (as described below). An inner diameter of the capillary used in the present invention may range from 1 μm to 100 μm. In particular, the diameter of the capillary may be at least 1, 2, 5, 10, 15, 20, 25, 30, 35, 40, 45, 50, 55, 60, 65, 70, 75, 80, 85, 90, 95 or 100 μm. Preferably, the capillary used in the present invention has a diameter of about 25 μm to 50 μm. The capillary may be made from fused silica. The length of the capillary used in the present invention may range from 1 cm to 50 cm. In particular, the capillary may be at least 1, 3, 5, 10, 12, 14, 16, 18, 20, 22, 24, 26, 28 or 30 cm in length. Preferably, the capillary used in the present invention is about 22 cm long.

As mentioned above, in one embodiment, the liquid jet may be generated by a co-flow method in which the liquid jet may be produced by stabilization through co-flow of a vapour sheath that surrounds the jet. The vapour sheath can be formed from helium or another inert gas (e.g. nitrogen, carbon dioxide or argon).

The liquid jet may be fed into the vacuum by the capillary used to produce the jet. The high pressure needed to drive the liquid through the thin capillary may be provided by an inert backing gas, such as argon, nitrogen or compressed air. This gas may be delivered through a pipe connection from a gas cylinder, preferably via a regulator.

Preferably, the apparatus comprises a substrate on which the product of the chemical reaction may be collected. The substrate is preferably maintained at a temperature of less than 173.15° C. (100 Kelvin). The substrate can be cooled before use, for example, by immersing it in liquid nitrogen, preferably until the liquid nitrogen has stopped boiling, or by connecting it to a liquid nitrogen bath cryostat or a closed-cycle refrigerator or a Peltier-refrigerator. The substrate may be metallic. Preferably, the substrate comprises stainless steel. The substrate may be substantially cylindrical, curved or planar in shape. The substrate preferably comprises an aperture extending through its forward facing surface, and through which the liquid jet may pass, so that the product of the chemical reaction collects on the rear inner surface of the substrate. The substrate may also be in an axial arrangement substantially perpendicular to the liquid jet. The substrate may also be in co-axial arrangement.

The reaction may take place between two or more atoms or atomic ions. However, preferably the apparatus is used to form a nanoparticle. The nanoparticle may comprise at least 10, 20, 30, 40 or 50 atoms or atomic ions. The nanoparticle may comprise at least 100, 200, 300, 400, 500, 600, 700, 800, 900, 1000 atoms or atomic ions.

The method may comprise forming the nanoparticle (i) on the surface of the liquid jet, (ii) within the surface layer of the liquid jet, (iii) within the deep bulk-volume of the liquid jet, or (iv) on the substrate. The method may comprise collecting the nanoparticle, preferably on the substrate.

The term "nanoparticle" can mean a particle having one or more dimensions at the nanometer scale, i.e. particles having one or more dimensions of between about 0.1 nm and about 1000 nm. The term "nanoparticle" can encompass both ultrafine particles (from about 1 nm to about 100 nm) and fine particles (from about 100 nm to about 500 nm). The average diameter of the nanoparticle may therefore be between 1 nm and about 1000 nm, between 1 nm and 750 nm, between 1 nm and 500 nm, between 1 nm and 250 nm or between 1 nm and 100 nm. Preferably, the average diameter of the nanoparticle is between 1 nm and about 50 nm, between 1 nm and 25 nm, between 1 nm and 15 nm, between 1 nm and 10 nm, or between 1 nm and 5 nm, or between 1 nm and 3 nm, or between 0.5 nm and 3 nm. Advantageously, the apparatus and method of the invention enable the creation of very small nanoparticles with desired properties. Preferably, the nanoparticles are stable in solution. Preferably, the nanoparticles do not require surfactants for stabilisation.

The apparatus and method may be used to produce a film of material comprising a plurality of nanoparticles. For example, $(Ag_nAu_m)_p$ where n, m and p can be any number equal to or greater than one. The thickness of the film may be at least 0.1, 0.2, 0.3, 0.4, 0.5, 0.6, 0.7, 0.8, 0.9, or 1 nm. The film may be in the form of amorphous nanoparticles, crystalline nanoparticles or multilayer.

The liquid jet also serves as a medium through which a surfactant may be added to prevent agglomeration of nanoparticles. Thus, the liquid jet may comprise a surfactant. The presence of a surfactant at a very early stage in the reaction process has the advantage that agglomeration of the nanoparticles is immediately prevented. Examples of surfactants that may be used include polyvinylpyrrolidone (PVP), oleic acid and citric acid.

A combination between gas-phase and wet liquid phase methods provides more degrees of freedom such that entirely new types of nanostructure may be produced.

Thus, in a third aspect, there is provided a nanoparticle obtained or obtainable by the apparatus according to the first aspect, or the method of the second aspect.

In particular, the nanoparticles produced by the apparatus or method of the present invention may have a different chemical composition or different size compared to prior art NPs. As a consequence, the electronic, chemical, magnetic and optical properties, including optical absorption properties, for example, of these new NPs will be different.

In fact, due to the present invention, the inventors have, for the first time, been able to produce fluorescent nanoparticles of silicon in different solvents, which remain stable for more than a year. In addition, the inventors noticed that the fluorescence spectrum of these nanoparticles differed depending upon the particular solvent used. This demonstrates that nanoparticles are sensitive to their chemical environment and means that, ultimately, NPs could be used to analyse the bio-chemical composition of different liquids. Moreover, the inventors have found that new types of nanoparticles produced by the apparatus or method of the present invention are able to align into a highly regular grid-shaped pattern when deposited on a graphite surface. The separation of the grid lines was in the order of 10 nm, which is promising for the production of micro-arrays and for use in the micro-structuring of materials.

According to a fourth aspect of the invention, there is provided the nanoparticle according to the third aspect, for use in therapy or diagnosis.

According to a fifth aspect, there is provided use of the nanoparticle according to the third aspect, in therapy, diagnosis or electronics.

Nanotechnology approaches to drug delivery centre on developing nanoparticles to improve drug bioavailability. In particular, nanoparticles encapsulating or conjugated to various therapeutic agents can improve efficacy and reduce toxicity through enhancement of specificity. The therapeutic agent may be a protein, peptide, chemical compound, genetic material (i.e. an oligonucleotide), small molecule or any other active molecule. NPs also have a high drug loading capacity, tend to be stable in aqueous environments over long periods of time, are non-toxic and non-immunogenic and may be targeted in vivo. In addition, they can avoid the body's defence mechanism. Where larger particles would have been cleared from the body, cells take up these nanoparticles because of their size. Many diseases depend upon processes within the cell and can only be impeded by drugs that make their way into the cell.

Furthermore, NPs can encapsulate or be conjugated to imaging agents so that they can be visualised non-invasively by magnetic resonance imaging (MRI), ultrasound, fluorescence imaging, confocal microscopy and the like. Suitable imaging agents include, for example, fluorine compounds, such as perfluorocarbon moieties (PFCs), and fluorescent labels, such as fluorescent dyes.

Therapeutic and imaging agents may be included in the NPs by any suitable means including encapsulation, covalent conjugation, physical immobilisation (for example, by electrostatic attraction, hydrophobic interaction and such like), layer-by-layer (LBL) adsorption and so on. The particular method used will depend upon the particular agent and the NPs selected, and such methodology would be within the remit of a skilled person.

Nanoparticles can be linked to biological molecules which can act as tags, to direct the nanoparticles to specific sites within the body or specific organelles within the cell both in vitro and in vivo, thus maximising bioavailability both at specific sites or over a period of time, or to follow and track the movement of individual protein, DNA or RNA molecules in living cells. Common tags are monoclonal antibodies, aptamers, streptavidin or peptides. These targeting agents should ideally be covalently linked to the nanoparticle and should be present in a controlled number per nanoparticles. Multivalent nanoparticles, bearing multiple targeting groups, cluster receptors, which can activate cellular signalling pathways, and give stronger anchoring. Monovalent nanoparticles, bearing a single binding site, avoid clustering and so are preferable for tracking the behaviour of individual proteins.

The use of nanoparticles in electronics means that the capabilities of electronic devices can be increased while at the same time their weight and power consumption can be decreased. For example, using NPs improves display screens on electronic devices, by reducing power consumption while at the same time decreasing the weight and thickness of the screens, increases the density of memory chips, and reduces the size of transistors used in integrated circuits.

Due to their large surface to volume ratio, which results in extensive exposure of their atoms or molecules to their environment, nanoparticles make good catalysts. Potential catalytic applications for nanoparticles include CO oxidation in combustion processes, hydrogen oxidation in fuel cells and methane conversion to methanol in the oil industry. However, as the aforementioned ratio changes so does the nanoparticle's electronic properties, as atoms or molecules at edge or vertex positions will have a lower coordination than their bulk-volume counterparts, which makes them more reactive. Consequently, surfaces covered with nanoparticles exhibit more reactive sites that flat surfaces not covered with the same. Moreover, as, in the quantum size regime, the addition or removal of just one atom, molecule, atomic ion or molecular ion from a nanoparticle can drastically change its reactivity, control of size is a powerful means to tune catalytic activity.

Nanoparticles could also be used to increase the efficiency of solar cells. Much of the light that passes current state of the art solar cells remains unused since the solar cells are too thin to collect it all. Nanoparticles show potential as light scatterers, as they could be used to direct the light into the photo-active region of the solar cell. Furthermore, the spectral sensitivity of a solar cell could be improved by using fluorescent nanoparticles to act as wavelength shifters, i.e. to absorb light in the UV spectral range and emit fluorescence that spectrally overlaps with the particular solar cell's absorption.

Nanoparticles have applications as anode material in Li-ion batteries. Silicon NPs store a large amount of Li atoms due to their ability to expand. This increases the performance of Li-batteries.

In a further aspect, there is provided an apparatus for carrying out a chemical reaction, the apparatus comprising a vacuum chamber containing gas, and feed means for feeding a liquid jet into the vacuum chamber and through the gas, wherein, in use, atoms and/or molecules of the gas react with each other and/or with atoms and/or molecules of the liquid jet, to thereby form a reaction product.

The apparatus may be configured to allow the atoms/molecules/atomic or molecular ions of the gas and/or liquid jet to react with each other.

In another aspect, the invention provides a method for carrying out a chemical reaction, the method comprising:
(i) providing a gas comprising atoms and/or molecules in a vacuum chamber;
(ii) feeding a liquid jet comprising atoms and/or molecules into the vacuum chamber and through the gas; and
(iii) allowing the atoms and/or molecules of the gas to react with each other and/or with the atoms and/or molecules of the liquid jet, so as to form a reaction product in the vacuum.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying diagrammatic drawings, in which.

EXAMPLES

The invention will now be described by way of illustration only in the following examples.

The inventors have developed a novel method for producing nanoparticles, which can be used in a wide variety of biomedical, optical and electronic applications. The method involves a combination between gas-phase and wet chemical methods for producing nanoparticles. However, the inventors found that combining these two types of method is very difficult, because metal or semiconductor vaporisation techniques require a vacuum and most liquids cannot exist at the low pressures required. This is because the co-existence of liquid and gas phases is governed by the vapour pressure curve. A liquid, for example water, put into vacuum would normally freeze if the pressure was lowered to that required for metal or semiconductor vapour generation.

Figure 1:
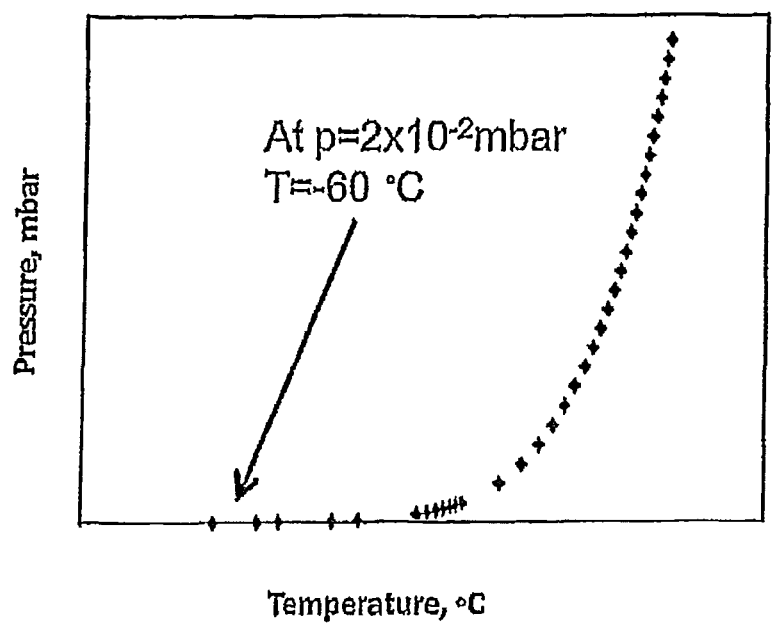
FIG. 1 illustrates a typical vapour pressure curve showing that the temperature of the liquid at low pressure is below the freezing point.

Referring to FIG. 1, there is shown a typical vapour pressure curve to illustrate the implications of the relationship between pressure and temperature. At a pressure of $2\times10^{-2}$ mbar (i.e. the pressure that is required to sputter silicon in a vacuum apparatus), the corresponding temperature of a liquid, such as water, would be below its freezing temperature. This shows that by whatever means liquid is introduced into a high or ultra-high vacuum, freezing at equilibrium conditions can be expected. The inventors, therefore, developed a novel apparatus which overcame these problems.

Example 1: Realisation of Prototype

In order to circumvent the problem that liquid put into a vacuum would normally freeze at the very low pressure required for metal or semiconductor vapour generation, the inventors decided to investigate using a jet of liquid. Such jets were first investigated in the 1980s in order to study microscopic properties of liquids using techniques that require vacuum. Examples are electron spectroscopy or soft x-ray scattering. Faubel and co-workers were the first to report the successful generation of liquid jets in vacuum (Faubel M et al. (1988) *Zeitschrift für Physik D Atoms* 10: 269) using turbulent flow using high hydrostatic pressures before a nozzle/capillary to gain Reynolds numbers above 2000. The technique by Faubel and co-workers has since then been adopted by other groups. The co-flow method has been adopted by Spence and co-workers (Weierstall U et al. (2008) *Experiments in Fluids* 44: 675). They have used a sheath of helium gas to establish a liquid jet of water. However, the use of helium imposes a great gas load on the vacuum pumps of the apparatus.

Using a liquid jet (26), however, the inventors were able to prevent freezing because the cooling rate was reduced and the liquid remained in a stable non-frozen state. Freezing only occurred after the liquid jet (26) had reached a cold target (4) where it was deposited. An important implication of using a liquid jet (26) is that it allows solutions to be delivered into the vacuum (24). Evaporation for example, was unable to achieve this as it separated solutes and solvents. Other methods, such as electrospray, had a very low throughput and charged the solutions as they broke up into droplets. The availability of a liquid jet (26), therefore, established a way of delivering solution into the vacuum (24) which significantly expanded the available range of reactions for nanostructure growth.

Hence, a prototype apparatus (20) was constructed by the inventors in order to demonstrate that a micro jet (26) was able to deliver the ingredients for nanostructure growth in the liquid state into a vacuum (24), while, at the same time, other processes that require vacuum, such as ion-sputtering, were unaffected. The inventors demonstrated the production of silicon, silver and iron nanoparticles.

Concept of Apparatus

Figure 2:
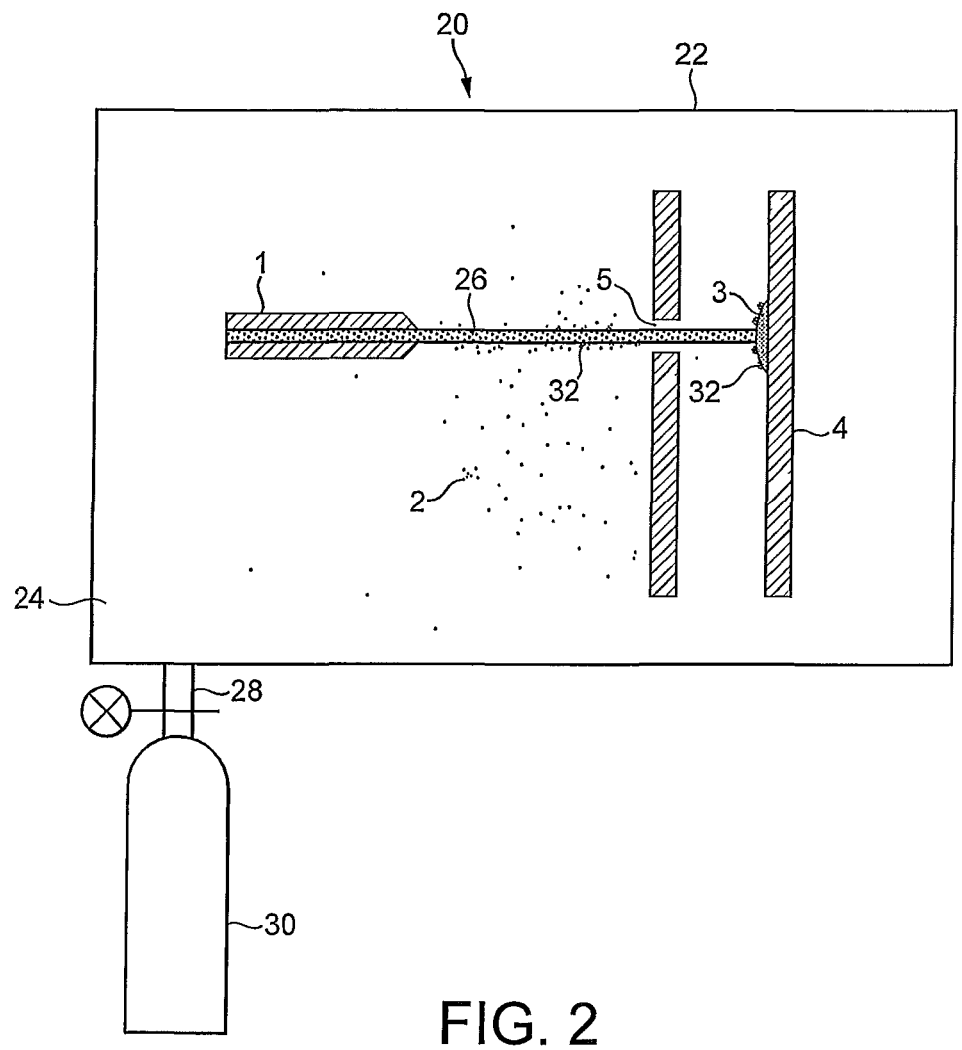
FIG. 2 illustrates a schematic representation of one embodiment of an apparatus comprising a liquid micro jet used to produce nanoparticles (NPs)

An apparatus (20) that fulfils the above requirements for the generation of nanoparticles (32) was designed, as shown in FIG. 2. The apparatus (20) includes a vacuum chamber (22) for containing a vacuum (24). The chamber (22) also contains a vapour (2), such as a metal or semiconductor vapour, achieved either thermally or by ion-sputtering, and a micro jet (26). Sputtering is a standard procedure to achieve vapours from metals or semiconductors (2) in the vacuum (24). In order to achieve sputtering, a sputtering gas was used, which was usually argon, and a sputtering target (66). Before the deposition of nanoparticles (32) on a cold target (4), an atmosphere of argon gas at a pressure of $2\times10^{-2}$ mbar was established in the vacuum chamber (22) by opening a gas inlet valve (28) connected to an argon cylinder (30). This pressure is usually sufficient to ignite sputtering, which means that the argon (Ar) atoms are ionised and strongly accelerated to a p-doped silicon target. The atomic gas of silicon is created in the vacuum (24) which is intersected by the liquid jet. The atoms collide with the liquid jet, as shown in FIG. 2.

Two liquid micro jet concepts were pursued: (i) a liquid filament stabilised through co-flow of a vapour sheath that surrounds the filament; and (ii) a micro jet driven at high pressures through a capillary so that the flow becomes turbulent. The turbulent nature of the flow would prevent the liquid from immediately freezing. The liquid filament generated in either of these ways had to intersect the metal or semiconductor vapour (2) and hit a liquid nitrogen-cooled target (4). Here, the components would freeze and stick until melted.

The literature reports liquid jets produced by the co-flow method using helium gas as a sheath (Weierstall U et al. (2008) *Experiments in Fluids* 44: 675). The inventors favour the use of different gases, for example carbon dioxide, since it is more cost effective and easier to pump, and in particular the vapour of the liquid itself. For example the use of water vapour to stabilise liquid filaments of water has the benefit of cost-efficient gas supply and the control of the temperature of the water filament through variation of the sheath density, or water vapour flux respectively.

FIG. 2 shows an embodiment of the apparatus (20) where a liquid jet (26) is generated using a heated micro capillary (1). The liquid jet (26) passes through metal or semiconductor vapour (2) and picks-up atoms from the vapour. The atoms have to have contact with the surface of the liquid jet in order to aggregate. The ingredients of the liquid jet (26) and the aggregated atoms stick and cluster (3) on a cold target (4), where the liquid melts upon heating. The cold target (4) is cylindrical and has a hole (5) for the micro jet (26) to enter and pass through.

The process of diffusion and sequential encounters will continue until a cluster of atoms is formed whose chemical reactivity is significantly smaller (a "passivated cluster"). The clusters formed in this way are chemically stable.

The liquid jet (26) also serves as a medium through which surfactants are added to prevent agglomeration of nanoparticles. Surfactants that are added in this way are readily available when the deposit on the cold target melts and when nanoparticles that have been formed gain mobility. The presence of surfactants at a very early stage has the advantage that agglomeration of the nanoparticles is immediately prevented.

The liquid jet (26) also delivers a solution that causes the surface of metal or semiconductor nanoparticles to react ("to passivate") so that a surface layer with distinct physical and chemical properties is formed. This is particularly important for the production of fluorescent core-shell semiconductor nanoparticles.

As can be seen from the above, the inventors have found that liquid micro jets (26) in vacuum (24) allow mixing of vapours (2), for example silicon, with other ingredients needed for the growth of NPs.

Extraction of Nanoparticles

Once formed the nanoparticles are carried within the liquid towards the cold target (4) where they stick and freeze together with the liquid. After deposition is finished the cold target (4) is warmed up, whereupon the ice melts, yielding liquid containing stable nanoparticles of the starting element. The nanoparticles tend to physically agglomerate within the liquid due to van der Waals type forces. However, clusters below a certain size have enough thermal energy to overcome physical attraction and, therefore, form a stable phase.

As shown in FIG. 2, in one embodiment, the cold target (4) consists of a stainless cylinder with a hole (5) in it to allow the liquid jet to penetrate inside. The purpose of the hole (5) is to increase the purity of the sample and the selectivity of the process. While the NPs fly through the hole (5) together with the liquid jet and freeze on the inner walls, the uncondensed atomic vapour will not make its way inside.

Before deposition and evacuation of the apparatus, the cylinder is immersed into liquid nitrogen. When the bath stops boiling, the temperature is sufficiently low and the cylinder is transferred to the vacuum apparatus.

One existing problem is that the liquid may freeze back from the cold target all the way to the capillary and block it. Way to prevent this include, for example, (i) use of a shallow impact angle, (ii) use of a 'chopper' wheel to cut ice fibres that may form in to pieces, and (iii) exploitation of Rayleigh-instabilities.

The throughput of nanoparticles (26) is limited by the flux of metal vapour (2) and the surface area of the liquid jet (26) in the condensation/reaction region and comparable to that of traditional thin film deposition techniques.

Growth Control by Liquid Filament Composition

The electronic (optical and magnetic properties, chemical reactivity etc.) and geometric properties (structure and nanoparticle size) of NPs depend on the physical and chemical properties of the liquid; therefore choice and chemical composition of the liquid are important. For example, the growth of silicon clusters will be inhibited by reaction with water, which causes an OH— group to form at the surface of the clusters. The majority of clusters that are formed by condensation of silicon atoms within the surface layer of a filament of water will, therefore, be very small. The size limit depends on the pH value and the addition of acids or bases will, accordingly, drive the average size up or down. The type of liquid also determines the maximum size of stable phase cluster achievable in a liquid as the attraction force (i.e. the Hamaker constant) is specific for every liquid. Liquids with large Hamaker constants will reinforce agglomeration of clusters and shift the size distribution of clusters that are stable against agglomeration towards the smaller end of the scale.

Growth Control by Serial or Parallel Arrangement/Production of Doped or Alloy Nanoparticles Clusters/nanoparticles consisting of element A and element B are formed in a parallel or serial arrangement of vapours. Serial arrangement, for instance first A then B, will force growth of clusters into a geometry with a core of A and a surface of B. Variation of the vapour density will produce core-shell clusters of, for example, equal quantities or, in the most extreme difference in concentration, a single atom of A in the centre of cluster B or a single atom B on the surface of cluster A. If vapours of A and B are generated within the same region (parallel arrangement) the liquid filament will pick up amounts of A and B proportional to the partial pressure thereby producing alloy clusters. By variation of the respective vapour pressure densities it will, therefore, be possible to produce nanostructures that range from defect-rich alloys to stoichiometric perfect alloys. The scheme can be expanded to produce compound nanoparticles consisting of A, B or C or more compounds.

Growth on Quasi-Solid Filaments

Lowering the hydrostatic pressure of the liquid forces the filament formation into a regime where quasi-solid/liquid fibres are grown. These fibres propagate much slower than the liquid filaments and it is straightforward to deposit vapours on the fibre's surface at a much higher rate than the growth rate of the fibres. In this way, solid fibres will be formed. The extraordinary high cooling rate provided through contact with the fibres produces preferentially amorphous structures.

Micropatterning Using the Liquid Jets

Depending on the diameter of the capillary used (see above), liquid filaments can be established with diameters down to 5 μm. By using an x-y piezo driven manipulator it will be possible to either steer the cold-head or the liquid jet in order to produce nanometer-sized patterns (with a resolution close to 5 μm) of nanoparticles on a substrate of choice.

Growth of Atomic Clusters on the Surface of Filaments

In such a set up the liquid jet can assume several roles. For instance, it serves as a medium in which atoms of metal or semiconductor vapours condense into clusters and in which these clusters are transported to the target. In particular, at the pressure present in the vacuum, the collision rate between atoms is too low to cause sufficiently high numbers of encounters that lead to bound states. The vapour itself does, therefore, not cause nanoparticles to grow. When an atom collides with the surface of the liquid filament it will be slowed down and become trapped due to the attractive forces of the liquid. Thereupon, the atom will diffuse until it encounters another atom with which it reacts into diatomic mode. The heat of reaction is efficiently absorbed by the liquid.

Figure 3:
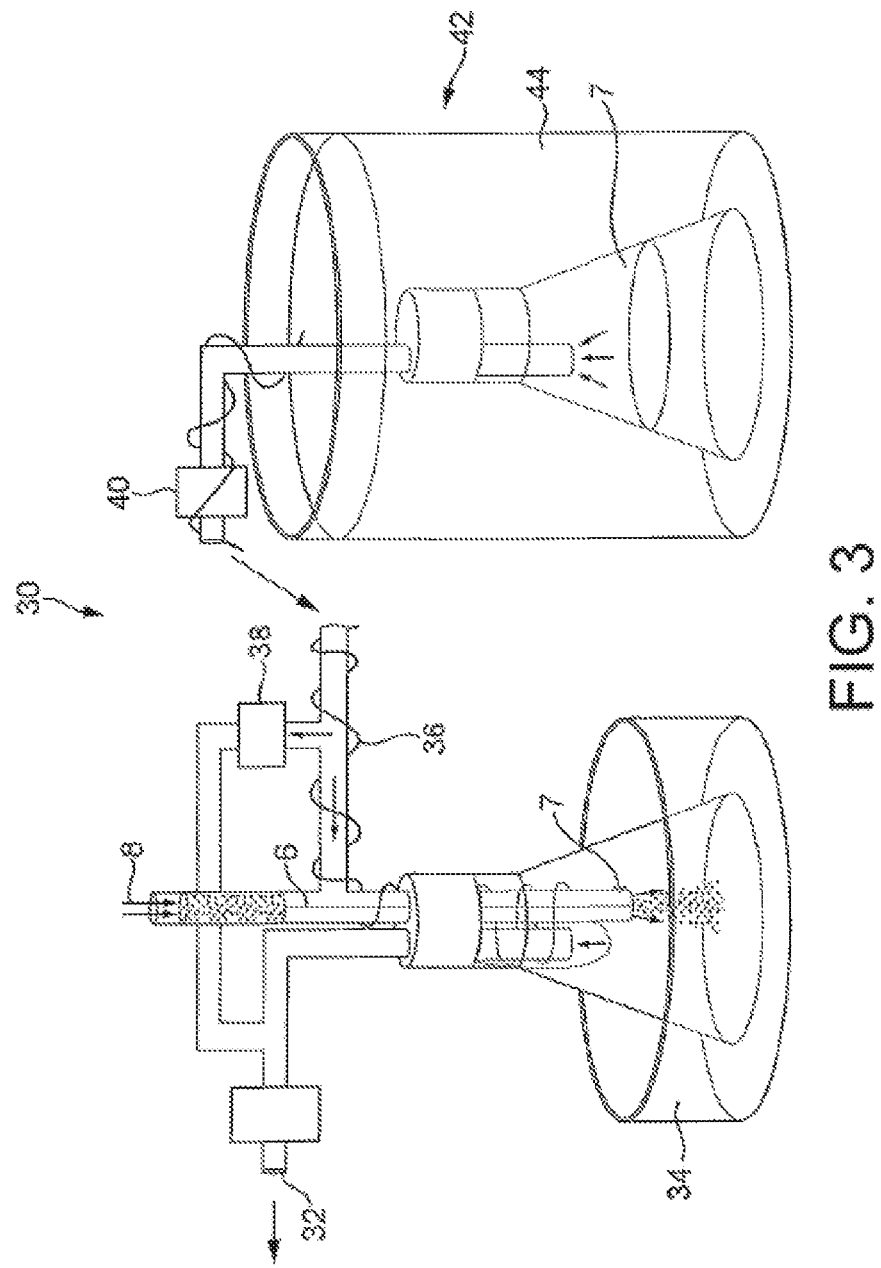
FIG. 3 illustrates an embodiment of a vacuum system consisting of glassware, rubber bungs and a scroll pump.
Figure 4:
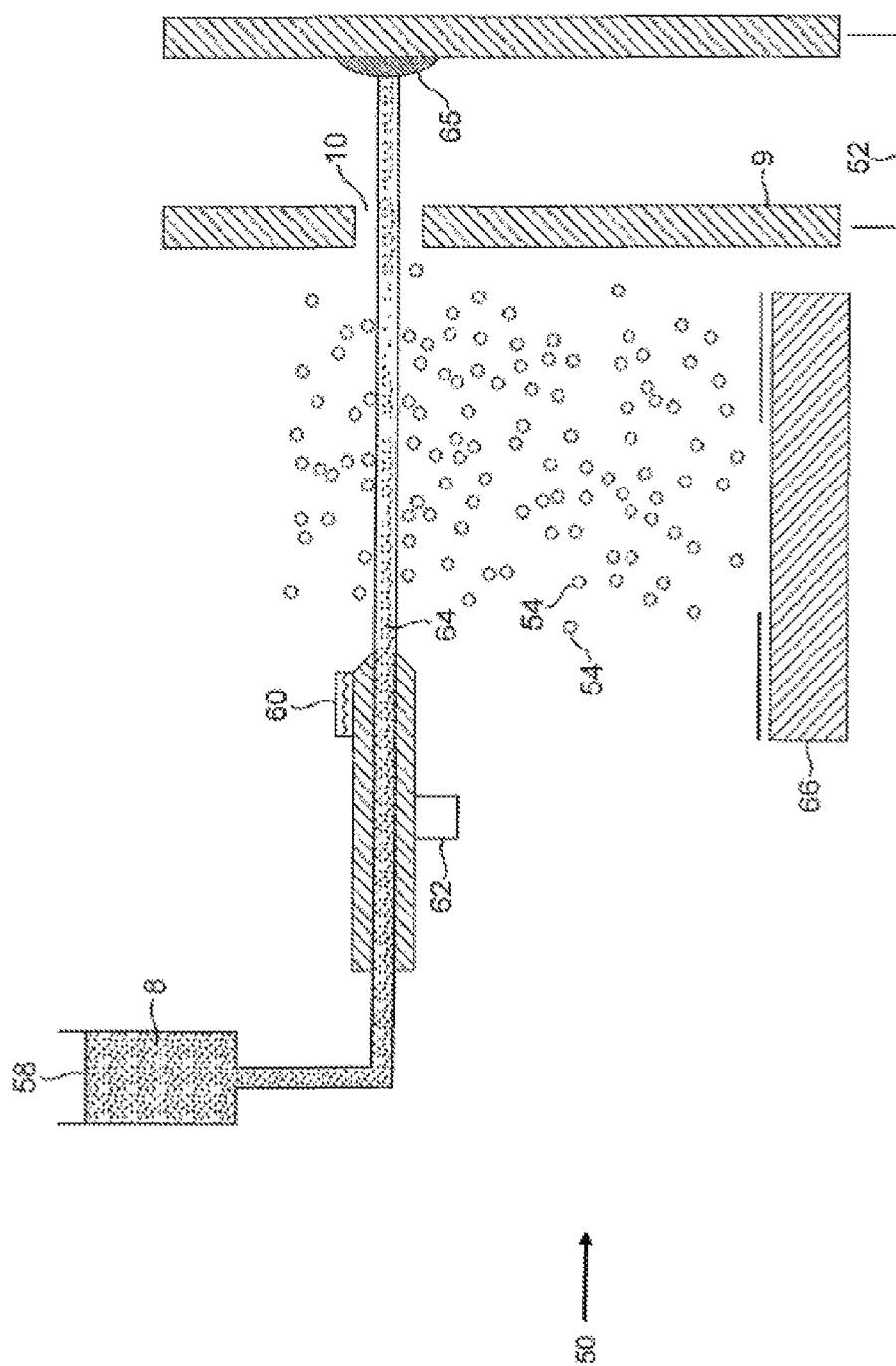
FIG. 4 illustrates an experimental setup for the generation of liquid jets, sputtering and co-deposition on a cold target.
Figure 5:
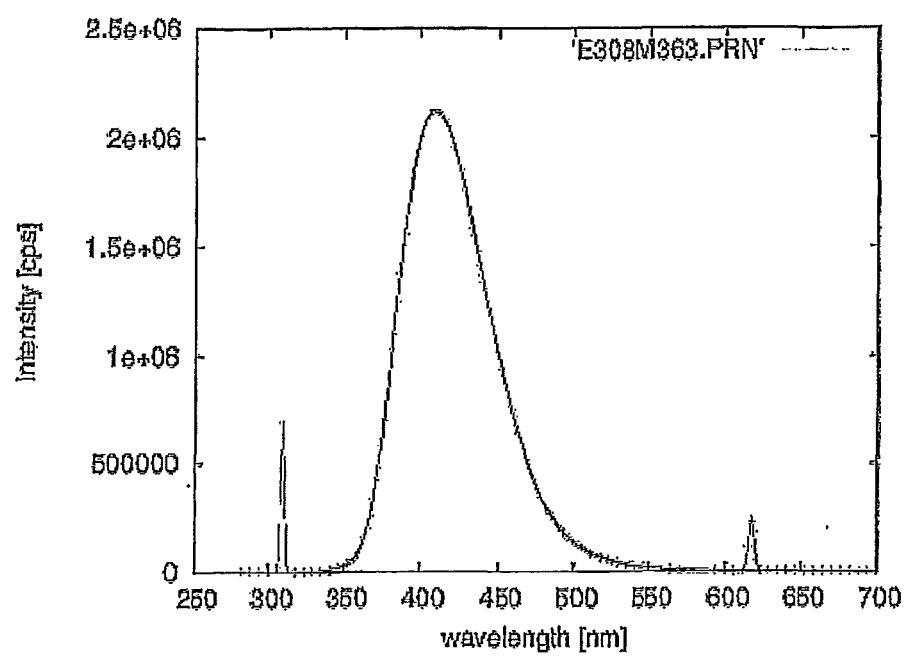
FIG. 5 illustrates the typical fluorescence spectrum of silicon nanoparticles in water produced using the apparatus and method of the present invention.

Preliminary tests of a liquid jet source design were first undertaken in air and then in vacuum (31) using a highly simplified vacuum system, as shown in FIG. 3, consisting of glassware, rubber bungs and a scroll pump. Two capillary set-ups, one using the co-flow, the other using the turbulent flow scheme were investigated. The minimum vacuum pressures that were achieved using this set-up were only in the range of 10-1 mbar but this was sufficient to test the set-up and to explore the relevant parameters. The use of glassware allowed for the inspection of the jet so that the inventors were able to realise quickly whether the jet was starting to freeze or not.

Referring to the apparatus of FIG. 3 (30), the capillary set-up consisted of off-the-shelf fused-silica capillaries (6) for chromatography applications of 25 and 50 μm diameter (Agilent). The capillaries were sealed within stainless steel pipes of 6 mm outer diameter using commercial ferules and fittings (Siltite) and connected to a reservoir (8) that contained the liquids. Towards the end of the liquid jet source a temperature sensor (7) and a heater were attached so that the temperature could be monitored and changed. The high pressures needed to drive the liquid through the thin capillaries were provided by inert backing gas which was delivered through a pipe connection from a gas cylinder via a regulator to the reservoir (8). The backing gas acted like a piston and provided variable pressures up to 200 bar in a simple fashion. A compressor was, therefore, not needed. The apparatus of FIG. 3 also comprised of a valve (32) to connect the system with a pump, a liquid nitrogen bath (34), a heating wire to prevent vapour condensation (36), further valves (38, 40), a water vapour source (42) and a water bath to reduce temperature fluctuations (44). The first test saw the "turbulent flow" version operate successfully and this concept was then further pursued.

After successful tests, the set-up was transferred into a commercial BOC Edwards thin-film Auto-Coater apparatus (50) in which metal or semiconductor vapours were to be generated by thermal evaporation or by ion beam sputtering, as shown in FIG. 2. The coater had to undergo a few modifications: electrical and gas feedthroughs were attached and a cold target was set up. A stainless steel cylinder (9) with a hole (10) extending there through served as the cold target, so that the liquid jet could reach the inside. It was, therefore, possible to collect the nanoparticles (NPs) much more selectively. Areas of the cylinder (9) which had been coated with the element used but had not been in contact with the liquid jet would not contribute to the sample since the sample was only collected from the deposit (65) that was melting from the inside of the cylinder. Before production of a sample, the cylinder (9) had to be immersed into liquid nitrogen to cool down. The apparatus (50) also comprised a petri dish for collection of samples in liquid form, after the ice had melted from the substrate (52), a source of high pressure argon to drive liquid through the micro capillary (58), a heater (60) and a thermocouple (62). Silicon is vaporised using argon ion sputtering of a silicon sputter target (66). Argon atoms become ionised in the electric field of the sputter head, the ions are then accelerated against the silicon target and silicon atoms and ions are sputtered off.

The liquid micro jet produced using the fused silica capillaries showed a number of advantageous properties: (i) the jet was highly collimated; (ii) the jet could be enabled and disabled by letting the capillary deliberately freeze or warm up by application of heat; (iii) the jet could be operated in different regimes depending on the temperature T and the hydrostatic pressure P of the liquid reservoir. Changes of P and T were found to turn the liquid jet from a filament into a divergent or collimated spray. Also the formation of long, continuous ice fibres was observed. In addition, (iv) the throughput was so high that after a few minutes samples of several milliliter were produced. The gas load of the pumps was moderate because of the high collimation of the jet which led to a high trapping efficiency.

Production of Nanoparticles

Silicon nanoparticles in water were produced as follows. First the reservoir was filled with water and the collector was cooled with liquid nitrogen. Then vacuum was established. Upon pumping the vacuum chamber the water at the end inside of the capillary froze. After a pressure sufficiently low to allow vaporisation of silicon by sputtering was reached the liquid jet was engaged. This was achieved by increasing the pressure of the argon backing pressure to about 20 to 60 bar, depending on the capillary in use, by subsequent heating of the end of the capillary for a short moment to melt the ice blocking the capillary. The liquid jet emerged thereupon and the sputtering process was started. After about 60 to 300 seconds a thick ice layer containing nanoparticles had been built inside the cylinder that collects the liquid jet and the process was stopped by switching-off the sputterer and by decreasing the argon backing pressure. Thereupon the vacuum apparatus was vented with inert gas, the collector was warmed-up, the ice melted and a liquid suspension containing the nanoparticles was collected in the petri dish.

The argon backing pressure was increased to a level at which a liquid jet established. Further increase would increase the throughput of liquid. The inventors found that the minimum backing pressure corresponded to a minimum velocity of the liquid within the capillary and a Reynolds number greater than 2000 as needed for turbulent flow. Therefore the chosen pressures depend strongly on the chosen geometry, i.e. the length and the diameter of the capillary and the dynamic viscosity of the liquid.

Example 2: Results

A number of samples were produced. It was decided to produce fluorescent silicon nanoparticles in water solution, as silicon clusters with water vapour had previously been achieved using an ultra-high vacuum machine (Brewer A et al. (2009) *Appl. Phys. Lett.* 94: 261102). However, the samples produced using the new method required much shorter production times (deposition of a few minutes) and showed a more intense fluorescence, with the fluorescence spectrum being similar. For the first time other liquids were investigated (isopropanol, ethanol), which each showed fluorescence at a wavelength different from water.

Variation of the working parameters of the liquid jet (26) showed a large range of different operation modes. Depending on the capillary temperature and the hydrostatic pressure the jet could be turned from a highly collimated filament into a spray and also into long, elastic and solid fibres when the liquid was freezing.

Coater

The experiments in the coater (50) allowed further tests to be performed to investigate the effect of capillary length on the formation of the liquid jet (26). In contrast to the glassware setup (20), the coater (50) allowed the inventors to use short capillaries. To be able to use sputtering, the freezing efficiency of the cold target (9) had to be high enough to maintain a pressure of $10^{-2}$ mbar. This was particularly important as previous experiments using a Knudsen beam of water revealed that sputtering of silicon was impossible due to the high pressure caused by the flux from the nozzle. A 6 cm long, 25 µm capillary was prepared and the formation of a liquid jet (26) tested. First, the co-flowing scheme was tested. The 50 µm capillary was tested as well, but this time high-pressure injection was used. Three samples of Si clusters were produced using high-pressure and the 50 µm capillary. The samples were investigated with photo fluorescence and UV/Vis absorption spectroscopy.

Freezing Efficiency of the Cold Target, Vapour Deposition Only

The automatic vacuum control in the Edwards coater (50) establishes a cycle of different pressures starting with a base pressure of $10^{-6}$ mbar. Sputtering requires argon at pressures of $10^{-2}$ mbar to be introduced into a vacuum system. At this pressure the turbo pump load is too high and a throttle is used. The water vapour valve was opened and vapour of a pressure $P_{vapour}$ (T=42° C.)=0.08 bar was passed through the outer orifice and was deposited on the cold target. During this procedure the apparatus showed pressure fluctuations ranging from $1.01 \times 10^{-3}$ to $2.6 \times 10^{-3}$ mbar. To increase the flux, the water vapour pressure was increased by increasing the temperature of the thermal vessel from 42° C. to 50° C. An increase in chamber pressure was expected; however, almost no changes were seen. The pressure inside the chamber fluctuated over the entire experiment. It was noted that the average pressure was always below the processing pressure of $10^{-2}$ mbar during sputtering. A layer of frozen ice on the surface of the cold target was seen, gradually growing thicker.

Liquid Jet, 25 µm Jet and Water Vapour Co-Flow

After demonstrating the effectiveness of the cold target (9), the aim was to operate the liquid jet using the co-flow method. The 25 µm capillary, shortened to 6 cm length, was fitted inside the nozzle of 0.4 mm internal diameter.

The expansion parameters (hydrostatic pressure, water vapour pressure) were varied but not in a systematic way. It is now known that the reason for the freezing of the water jet using the co-flow scheme lay, not in the wrong choice in the expansion parameters, but rather in the geometry of the capillary and the nozzle.

25 μM Ice Fibre

At different times, using the 25 μm and 6 cm long capillary, growth of long ice fibres was observed. The ice fibres were several centimeters long and some of them grew to the base plate of the apparatus; where they bent under the force of gravity. The growth of ice fibres was observed when the hydrostatic pressure was as low as 1 bar. Increasing the pressure further up to 20 bars caused the ice fibres to grow at a greater rate. The precise reason for this phenomenon remains unclear, but the inventors suspect that pinching of the capillary caused by being fitted too tightly may be important.

High Pressure Jets: 50 μM Water Jet

The initial failure in using the 25 μm capillary to produce liquid jets encouraged the inventors to increase the diameter and to investigate the high-pressure mode. The larger diameter was expected to reduce freezing of the liquid jet because the thicker gas sheath surrounding larger liquid filaments reduced the cooling efficiency. The 50 μm and 8 cm long capillary was used. At the beginning, it was very difficult to evacuate the coater (50) due to the higher flux from the larger capillary. A procedure was developed: first, the capillary was left to freeze, second, the coater was evacuated, third, the front part of the capillary was heated so that the blocked capillary would eventually open and allow a liquid jet to establish. The hydrostatic pressure was then slowly increased. At 20 bars the capillary started jetting.

The liquid jet (26) was found to abruptly change its direction within an angle of about 15 degrees. It was also observed that when the liquid filament touched the edge of the hole in the cold target it immediately froze, the ice growing quickly back towards the nozzle and blocking the entire jet. To prevent this effect we increased the diameter of the hole in the cold target and we decreased the distance between the cold target (9) and the capillary. These changes proved to be successful.

Variety of Samples

Three samples of silicon nanoparticles were produced: one with vapour deposition (A. Brewer and K von Haeften, *Appl. Phys. Lett.* (2009)), and the other two using the high-pressure liquid jet of the present invention. The deposition parameters of these samples are shown in Table 1.

Further Experiment Using 25 μm Capillary

The inventors' success using liquid micro-jets for the production of fluorescent NPs encouraged them to revisit the previous experiments with the 25 μm capillary, because using smaller capillaries would reduce the gas load. They investigated pinching of the capillary, systematically varying the torque of the fitting nut. The test was performed in ambient atmosphere and it was quickly discovered that the flux was correlated with torque confirming that pinching was possible. It was realised that by loosening the fitting nuts, liquid jets were achieved. Subsequent experiments were performed in vacuum and likewise liquid filaments were established. Furthermore, the length of the capillary was shortened once again to 25 mm, which was found to give better control of deliberate freezing and defrosting of the water in the capillary.

While operating the 25 μm capillary in vacuum, different height profiles of the deposited water were observed. In contrast to the 50 μm capillary, it seemed to provide much better control of the location of the frozen deposit, and also a narrow angular distribution. A variety of samples using water and other solvents (ethanol and isopropanol) were produced using the 25 μm capillary. All showed photo fluorescence.

While the sputtering power and deposition time were almost constant, it was observed that the fluorescence intensities of the samples produced with the 50 μm capillary were higher than those produced using the 25 μm filament. This effect was tentatively assigned to a different concentration of the samples potentially caused by the different surface area of the liquid filaments. Further experiments are needed to verify this hypothesis.

Figure 6:
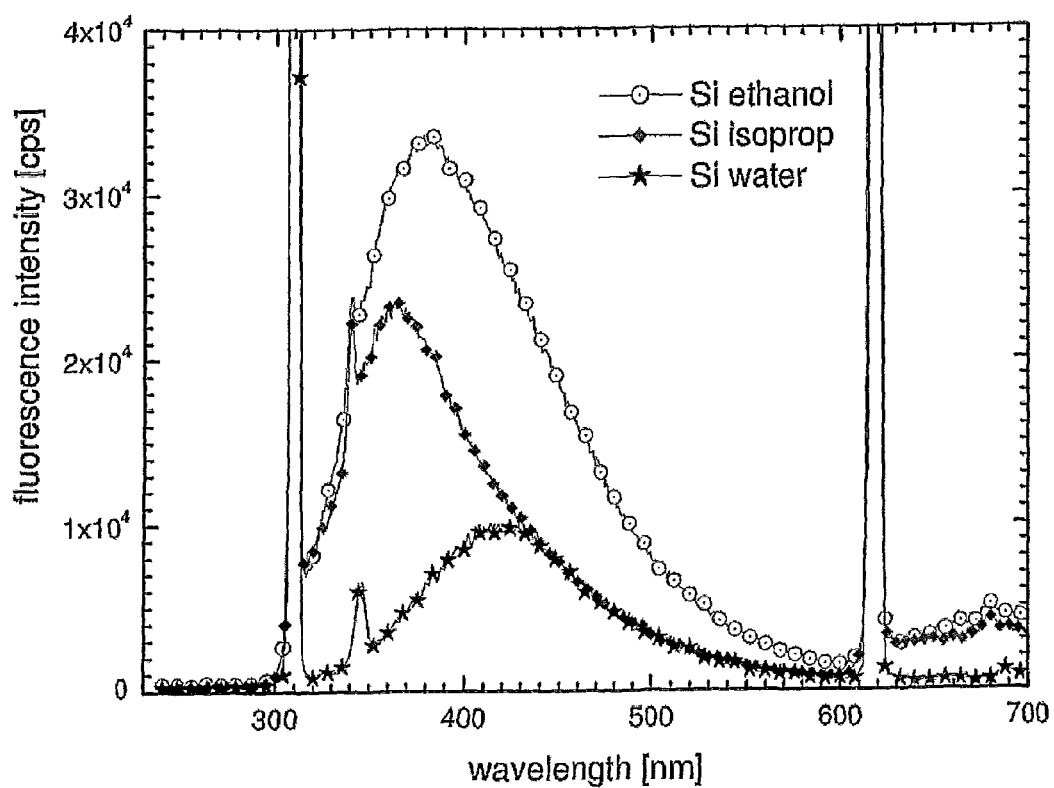
FIG. 6 illustrates the typical fluorescence spectra of silicon nanoparticles that have been produced using the apparatus and method of the present invention using liquid jets comprising water, ethanol and isopropanol.

FIG. 6 illustrates the typical fluorescence spectra of silicon nanoparticles that have been produced using the apparatus and method of the present invention using liquid jets comprising water, ethanol and isopropanol. Each of the aforementioned solvents has a distinct dipole moment. Similarities and differences can be seen in the fluorescence spectrum. Each spectrum shows a prominent fluorescent band of similar shape but with different peak fluorescence. Therefore, it is possible to use the nanoparticles to detect different solvents. In the case of water, ethanol and isopro-

TABLE 1

Three samples produce with two deposition methods

| | Operation mode | Temperature of water ° C. | Hydrotatic pressure, bar | Deposition time, min | Discharge power, W |
|---|---|---|---|---|---|
| sample 1 | vapour | 58 | 0.18 | 14 | 53 |
| sample 2 | high-pressure jet | 34 | 20 | 0.5 | 53 |
| sample 3 | high-pressure jet | 38 | 20 | 3 | 53 |

After deposition, the chamber was vented with nitrogen gas and the cold target (9) was left to defrost. The chamber was opened and the sample was collected from the petri dish using a glass pipette and bottled.

Fluorescence

A typical fluorescence spectrum for silicon nanoparticles in water produced in accordance with the apparatus and method of the present invention is shown in FIG. 6. The excitation wavelength was 308 nm. The spectrum shows broad fluorescence features with a prominent band peaking at 420 nm. The spectral shape is almost identical to that of samples produced earlier using the cluster and water vapour deposition method. However, the fluorescence intensity is increased.

panol, the peak fluorescence is also correlated with the dipole moment of the particular solvent used.

Figure 7:
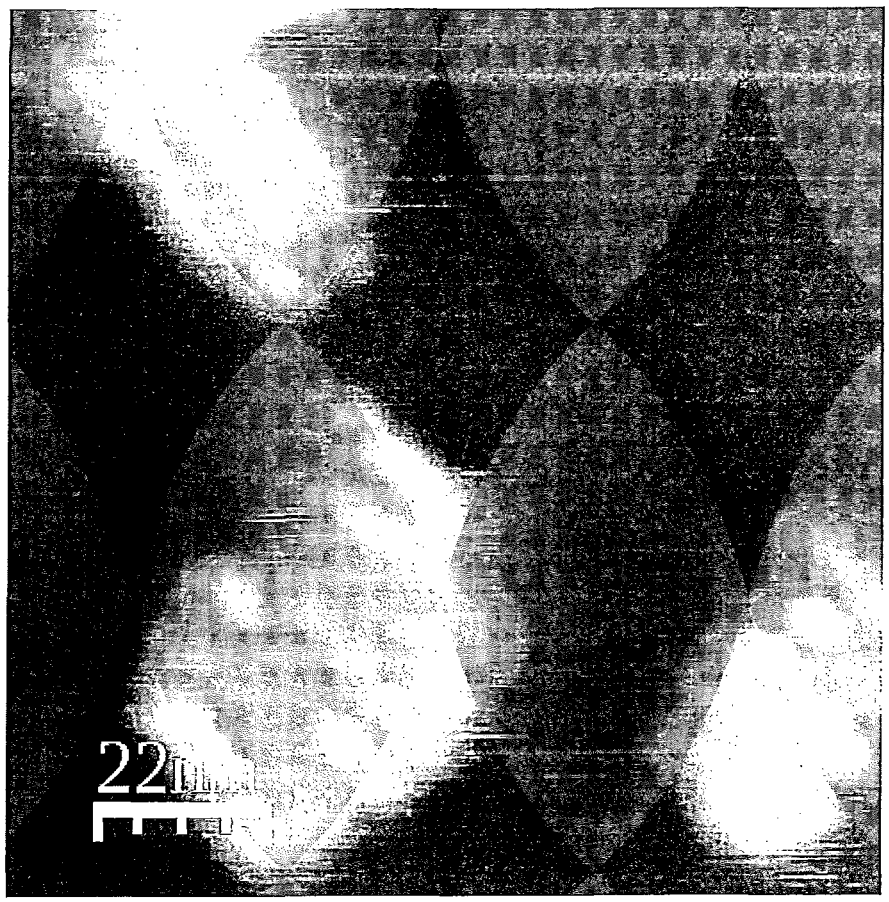
FIG. 7 shows actual silicon nanoparticles produced using the apparatus and method of the present invention using a liquid jet comprising water.

FIG. 7 shows actual silicon nanoparticles produced using the apparatus and method of the present invention and using a liquid jet comprising water. The resulting nanoparticle—water solution was drop-cast onto freshly cleaved highly oriented pyrolytic graphite (HOPG) crystals, subsequently vacuum dried and then investigated by atomic force microscopy (AFM). The image shows that the nanoparticles self-arrange into arrays. This behaviour is of importance for structural control on the nanometer size scale, for example in microelectronics, where known state of the art structuring methods have reached their physical limits.

Figure 8:
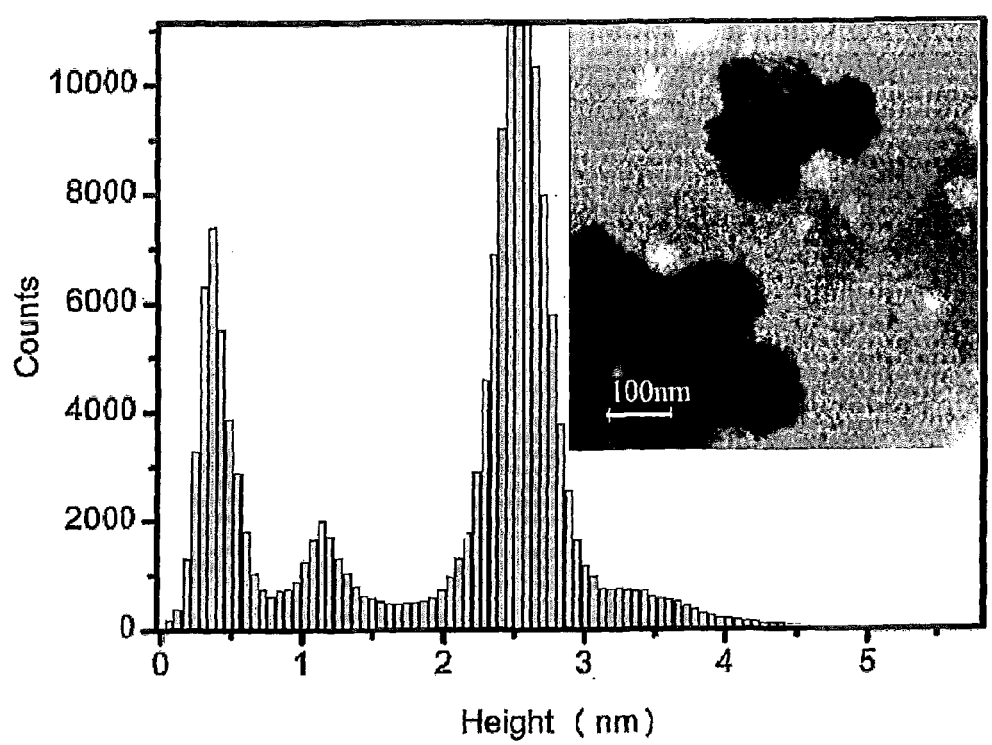
FIG. 8 shows films of silicon nanoparticles that were produced in the same way as the nanoparticles shown in FIG. 7.

FIG. 8 shows a 500×500 nm image of a HOPG substrate covered with several layers of agglomerated Si clusters that were produced in ethanol jets as well as the corresponding height distribution of the clusters after WSxM software image processing. Empty HOPG areas corresponding to the first peak in the height profile serve as a height reference. The second and third peaks correspond to single and double cluster layers, respectively. Islands belonging to the third cluster layer can be seen as well, but the number of counts is too small to significantly contribute to the histogram. Determination of a reference baseline is difficult over the whole image because of variations of the vertical elongation of the piezo scanner caused by thermal drift, thus reducing accuracy when determining the height of different clusters. However, the height profile shows unambiguously that mainly small clusters are produced, the height difference of 1.4 nm between the second and first layers providing a measure of the average cluster diameter.

In another experiment, it was attempted to coat iron NPs in chloroform solution with silicon, as this would allow a pathway for further functionalisation. This experiment was conducted using silicon sputtering and expansion of chloroform solution through a capillary. Optical inspection revealed that the iron nanoparticles had changed their surface but the microscopic characterisation is still underway.

SUMMARY

The apparatus and method described herein provide a new and flexible way to produce nanostructures or nanoparticles (NPs) with new properties. The method has the potential to be expanded using several micro jets and more sophisticated gas phase arrangements, for example:
1. One simple way of structuring samples is to "write" structures on a surface by moving the surface on an x-y-piezo manipulator. The resolution of such structures should be related to the liquid jet diameter. Long term, it should be possible to "jet-print" nanostructures onto a substrate by applying reactive components locally onto said substrate.
2. The combination of micro-fluidics and metal or semiconductor vaporisation will make the doping of single atoms onto NPs possible in batch processes. Important applications are catalysis and optical properties.
3. Shock-freezing of iron onto cold liquid beams may be suitable as a route towards the production of amorphous steel-microwires.

The invention claimed is:

1. An apparatus for forming a nanoparticle, the apparatus comprising:
    a vacuum chamber containing gas,
    feed means for feeding a liquid jet in the form of a liquid filament into the vacuum chamber and through the gas, and
    a substrate for collecting the nanoparticle,
    wherein in use, atoms and/or molecules and/or atomic and/or molecular ions of the gas collide with the jet and react with each other and/or with atoms and/or molecules of the liquid jet, to thereby form the nanoparticle.

2. An apparatus as claimed in claim 1, wherein the vacuum chamber is at a pressure of between about $10^{-12}$ and 1 mbar.

3. An apparatus as claimed in claim 1, wherein the gas is in the form of a vapour or a plasma in the vacuum chamber.

4. An apparatus as claimed in claim 3, wherein the vapour is a metal vapour, semiconductor vapour, molecular vapour or cluster vapour or the plasma is an electron plasma, ionic plasma, or ion vapour.

5. An apparatus as claimed in claim 4, wherein:
    (a) the metal vapour comprises or is formed from a transition metal, lanthanide or noble metal;
    (b) the semiconductor vapour comprises or is formed from a group IV element, a group III element reacted with a group V element, or a group II element reacted with a group VI element;
    (c) the semiconductor vapour comprises or is formed from carbon, silicon, geranium, tin, lead, BN, BP, AN, GaN, GaP, GaSb, InN, InP, ZnO, ZnS, ZnSe, CdS, CdSe or CdTe;
    (d) the molecular vapour comprises or is formed from $O_2$, $N_2$, $CO$, $CO_2$, $H_2O$, $NaCl$, $Mg_2O_2$ or $Al_2O_3$; and/or
    (e) the cluster vapour comprises or is formed from metal clusters such as $Fe_n$ or $Ag_n$, or semiconductor clusters, such as $Si_n$, $(GaAs)_n$ or $(CdS)_n$ that have been performed in another process.

6. An apparatus as claimed in claim 1, wherein the gas or vapour is produced by heating, laser ablation, sputtering, arcs, or discharges.

7. An apparatus as claimed in claim 1, wherein the liquid jet comprises or is formed from a polar or non-polar solvent.

8. An apparatus as claimed in claim 7, wherein the solvent comprises water, acetic acid, pentane, hexane, heptane, cyclohexane, methanol, isopropanol, n-propanol, ethanol, dichloromethane, acetonitrile, dimethyl sulfoxide, toluene, chloroform, pyridine, benzene, hydrogen, nitrogen, helium, neon, argon, krypton or xenon.

9. An apparatus as claimed in claim 1, wherein the hydrostatic pressure of the liquid jet is up to about 200 bar.

10. An apparatus as claimed in claim 1, wherein the liquid jet comprises a solution or a suspension.

11. An apparatus as claimed in claim 1, wherein one or more liquid jets or gases delivering different chemicals simultaneously is fed into the vacuum chamber.

12. An apparatus as claimed in claim 1, wherein the liquid jet is produced by passing the liquid through a capillary, using turbulent flow or using co-flow.

13. An apparatus as claimed in claim 12, wherein an inner diameter of the capillary is from 1 μm to 100 μm.

14. An apparatus as claimed in claim 1, wherein the liquid jet is produced by a co-flow method in which a vapour sheath surrounds the jet, and wherein the vapour sheath is formed from an inert gas, helium, nitrogen, carbon dioxide or argon.

15. An apparatus as claimed in claim 12, wherein an inert backing gas provides the force needed to drive the liquid through the capillary, and wherein the inert backing gas is argon, nitrogen or compressed air.

16. An apparatus as claimed in claim 1, wherein the substrate is metallic and maintained at a temperature of less than 173.15° C.

17. An apparatus as claimed in claim 1, wherein the substrate is substantially cylindrical, curved or planar in shape, and comprises an aperture extending through a forward facing surface through which the liquid jet passes.

18. An apparatus as claimed in claim 1, wherein the substrate is in an axial arrangement substantially perpendicular to the liquid jet.

19. An apparatus as claimed in claim 1, wherein the nanoparticle is formed on the surface of the liquid jet, within the surface layer of the liquid jet, within the deep bulk-volume of the liquid jet, or on the substrate.

20. An apparatus as claimed in claim 1, wherein the liquid jet comprises a surfactant, and wherein the surfactant is polyvinylpyrrolidone (PVP), oleic acid or citric acid.

21. A method for forming a nanoparticle, the method comprising:
(i) providing a gas comprising atoms and/or molecules and/or atomic and/or molecular ions in a vacuum chamber;
(ii) feeding a liquid jet, in the form of a liquid filament, comprising atoms and/or molecules into the vacuum chamber and through the gas;
(iii) allowing the atoms and/or molecules and/or atomic and/or molecular ions of the gas to react with each other and/or with the atoms and/or molecules of the liquid jet, so as to form the nanoparticle; and
(iv) collecting the nanoparticle on a substrate.

22. The method as claimed in claim 21, wherein the gas is in the form of a vapour or a plasma in the vacuum chamber, and wherein the vapour is a metal vapour, semiconductor vapour, molecular vapour, or cluster vapour or the plasma is an electron plasma, ionic plasma, or ion vapour.

\* \* \* \* \*